United States Patent
Magnuson

(10) Patent No.: US 8,377,092 B2
(45) Date of Patent: Feb. 19, 2013

(54) EMBOLIC PROTECTION DEVICE

(75) Inventor: Mark A. Magnuson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 925 days.

(21) Appl. No.: 11/520,109

(22) Filed: Sep. 13, 2006

(65) Prior Publication Data
US 2007/0066991 A1 Mar. 22, 2007

Related U.S. Application Data

(60) Provisional application No. 60/718,171, filed on Sep. 16, 2005.

(51) Int. Cl.
*A61M 29/00* (2006.01)
(52) U.S. Cl. ............................................. 606/200
(58) Field of Classification Search .................. 606/191, 606/192, 194, 198, 200; 623/1.11
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A | 12/1985 | Koehler | |
| 4,604,094 A | 8/1986 | Shook | |
| 4,619,246 A | 10/1986 | Molgaard-Nielsen et al. | |
| 4,643,184 A | 2/1987 | Mobin-Uddin | |
| 4,646,736 A | 3/1987 | Auth | |
| 4,650,472 A | 3/1987 | Bates | |
| 4,665,906 A | 5/1987 | Jervis | |
| 4,669,464 A | 6/1987 | Sulepov | |
| 4,688,553 A | 8/1987 | Metals | |
| 4,723,549 A | 2/1988 | Wholey et al. | |
| 4,727,873 A | 3/1988 | Mobin-Uddin | |

(Continued)

FOREIGN PATENT DOCUMENTS

DE 3429850 A1 2/1986
EP 1127556 A2 8/2001

(Continued)

OTHER PUBLICATIONS

Rubicon Embolic Filter, The Next Generation of EM, Rubicon Medical, www.rubiconmed.com.

(Continued)

*Primary Examiner* — Ryan Severson
*Assistant Examiner* — David Eastwood
(74) *Attorney, Agent, or Firm* — Brinks Hofer Gilson & Lione

(57) ABSTRACT

An embolic protection device includes a basket formed from flexible struts. The struts extend from a first end of the basket to the second end of the basket. The struts form a middle portion of the basket where the struts extend substantially perpendicular to a longitudinal axis, running between the first and second end of the basket.

18 Claims, 8 Drawing Sheets

U.S. PATENT DOCUMENTS

| | | |
|---|---|---|
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A * | 3/1992 | Fearnot ............... 606/159 |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |

| Patent | Kind | Date | Inventor |
|---|---|---|---|
| 6,096,070 | A | 8/2000 | Ragheb et al. |
| 6,099,549 | A | 8/2000 | Bosma et al. |
| 6,106,497 | A | 8/2000 | Wang |
| 6,126,672 | A | 10/2000 | Berryman et al. |
| 6,126,673 | A | 10/2000 | Kim et al. |
| 6,129,739 | A | 10/2000 | Khosravi |
| 6,136,016 | A | 10/2000 | Barbut et al. |
| 6,146,396 | A | 11/2000 | Konya et al. |
| 6,146,404 | A | 11/2000 | Kim et al. |
| 6,152,931 | A | 11/2000 | Nadal et al. |
| 6,152,946 | A | 11/2000 | Broome et al. |
| 6,152,947 | A | 11/2000 | Ambrisco et al. |
| 6,156,061 | A | 12/2000 | Wallace et al. |
| 6,156,062 | A | 12/2000 | McGuinness |
| 6,159,230 | A | 12/2000 | Samuels |
| 6,165,179 | A | 12/2000 | Cathcart et al. |
| 6,165,198 | A | 12/2000 | McGurk et al. |
| 6,165,199 | A | 12/2000 | Barbut |
| 6,165,200 | A | 12/2000 | Tsugita et al. |
| 6,168,579 | B1 | 1/2001 | Tsugita et al. |
| 6,168,603 | B1 | 1/2001 | Leslie et al. |
| 6,168,610 | B1 | 1/2001 | Marin et al. |
| 6,168,622 | B1 | 1/2001 | Mazzocchi |
| 6,171,327 | B1 | 1/2001 | Daniel et al. |
| 6,171,328 | B1 | 1/2001 | Addis |
| 6,174,318 | B1 | 1/2001 | Bates et al. |
| 6,179,851 | B1 | 1/2001 | Barbut et al. |
| 6,179,859 | B1 | 1/2001 | Bates et al. |
| 6,179,860 | B1 | 1/2001 | Fulton, III et al. |
| 6,179,861 | B1 | 1/2001 | Khosravi et al. |
| 6,187,025 | B1 | 2/2001 | Machek |
| 6,193,739 | B1 | 2/2001 | Chevillon et al. |
| 6,203,561 | B1 | 3/2001 | Ramee et al. |
| 6,206,931 | B1 | 3/2001 | Cook et al. |
| 6,214,025 | B1 | 4/2001 | Thistle et al. |
| 6,214,026 | B1 | 4/2001 | Lepak et al. |
| 6,221,091 | B1 | 4/2001 | Khosravi |
| 6,224,620 | B1 | 5/2001 | Maahs |
| 6,231,588 | B1 | 5/2001 | Zadno-Azizi |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,241,746 | B1 | 6/2001 | Bosma et al. |
| 6,245,012 | B1 | 6/2001 | Kleshinski |
| 6,245,087 | B1 | 6/2001 | Addis |
| 6,245,088 | B1 | 6/2001 | Lowery |
| 6,245,089 | B1 | 6/2001 | Daniel et al. |
| 6,251,092 | B1 | 6/2001 | Qin et al. |
| 6,251,122 | B1 | 6/2001 | Tsukernik |
| 6,254,550 | B1 | 7/2001 | McNamara et al. |
| 6,254,633 | B1 | 7/2001 | Pinchuk et al. |
| 6,258,026 | B1 | 7/2001 | Ravenscroft et al. |
| 6,258,115 | B1 | 7/2001 | Dubrul |
| 6,258,120 | B1 | 7/2001 | McKenzie et al. |
| 6,261,305 | B1 | 7/2001 | Marotta et al. |
| 6,264,672 | B1 | 7/2001 | Fisher |
| 6,267,776 | B1 | 7/2001 | O'Connell |
| 6,267,777 | B1 | 7/2001 | Bosma et al. |
| 6,273,900 | B1 | 8/2001 | Nott et al. |
| 6,273,901 | B1 | 8/2001 | Whitcher et al. |
| 6,277,125 | B1 | 8/2001 | Barry et al. |
| 6,277,126 | B1 | 8/2001 | Barry et al. |
| 6,277,138 | B1 | 8/2001 | Levinson et al. |
| 6,277,139 | B1 | 8/2001 | Levinson et al. |
| 6,280,451 | B1 | 8/2001 | Bates et al. |
| 6,287,321 | B1 | 9/2001 | Jang |
| 6,290,710 | B1 | 9/2001 | Cryer et al. |
| 6,299,604 | B1 | 10/2001 | Ragheb et al. |
| 6,306,163 | B1 | 10/2001 | Fitz |
| 6,309,399 | B1 | 10/2001 | Barbut et al. |
| 6,312,444 | B1 | 11/2001 | Barbut |
| 6,319,268 | B1 | 11/2001 | Ambrisco et al. |
| 6,325,815 | B1 | 12/2001 | Kusleika et al. |
| 6,325,816 | B1 | 12/2001 | Fulton, III et al. |
| 6,328,755 | B1 | 12/2001 | Marshall |
| 6,331,183 | B1 | 12/2001 | Suon |
| 6,331,184 | B1 | 12/2001 | Abrams |
| 6,334,864 | B1 | 1/2002 | Amplatz et al. |
| 6,336,934 | B1 | 1/2002 | Gilson et al. |
| 6,338,739 | B1 | 1/2002 | Datta et al. |
| 6,340,364 | B2 | 1/2002 | Kanesaka |
| 6,342,062 | B1 | 1/2002 | Suon et al. |
| 6,342,063 | B1 | 1/2002 | DeVries et al. |
| 6,344,048 | B1 | 2/2002 | Chin et al. |
| 6,344,049 | B1 | 2/2002 | Levinson et al. |
| 6,346,116 | B1 | 2/2002 | Brooks et al. |
| 6,348,041 | B1 | 2/2002 | Klint |
| 6,348,063 | B1 | 2/2002 | Yassour et al. |
| 6,350,271 | B1 | 2/2002 | Kurz et al. |
| 6,355,051 | B1 | 3/2002 | Sisskind et al. |
| 6,358,228 | B1 | 3/2002 | Tubman et al. |
| 6,361,545 | B1 | 3/2002 | Macoviak et al. |
| 6,361,546 | B1 | 3/2002 | Khosravi |
| 6,361,547 | B1 | 3/2002 | Hieshima |
| 6,364,895 | B1 | 4/2002 | Greenhalgh |
| 6,364,896 | B1 | 4/2002 | Addis |
| 6,368,338 | B1 | 4/2002 | Konya et al. |
| 6,371,961 | B1 | 4/2002 | Osborne et al. |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,379,374 | B1 | 4/2002 | Hieshima et al. |
| 6,380,457 | B1 | 4/2002 | Yurek et al. |
| 6,383,146 | B1 | 5/2002 | Klint |
| 6,383,171 | B1 | 5/2002 | Gifford et al. |
| 6,383,174 | B1 | 5/2002 | Eder |
| 6,383,193 | B1 | 5/2002 | Cathcart et al. |
| 6,383,196 | B1 | 5/2002 | Leslie et al. |
| 6,383,205 | B1 | 5/2002 | Samson et al. |
| 6,383,206 | B1 | 5/2002 | Gillick et al. |
| 6,391,044 | B1 | 5/2002 | Yadav et al. |
| 6,391,045 | B1 | 5/2002 | Kim et al. |
| 6,391,052 | B2 | 5/2002 | Buirge et al. |
| 6,395,014 | B1 | 5/2002 | Macoviak et al. |
| 6,402,771 | B1 | 6/2002 | Palmer et al. |
| 6,402,772 | B1 | 6/2002 | Amplatz et al. |
| 6,409,742 | B1 | 6/2002 | Fulton, III et al. |
| 6,413,235 | B1 | 7/2002 | Parodi |
| 6,416,530 | B2 | 7/2002 | DeVries et al. |
| 6,419,686 | B1 | 7/2002 | McLeod et al. |
| 6,423,052 | B1 | 7/2002 | Escano |
| 6,423,086 | B1 | 7/2002 | Barbut et al. |
| 6,425,909 | B1 | 7/2002 | Dieck et al. |
| 6,428,557 | B1 | 8/2002 | Hilaire |
| 6,428,558 | B1 | 8/2002 | Jones et al. |
| 6,428,559 | B1 | 8/2002 | Johnson |
| 6,432,122 | B1 | 8/2002 | Gilson et al. |
| 6,436,112 | B2 | 8/2002 | Wensel et al. |
| 6,436,120 | B1 | 8/2002 | Meglin |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |
| 6,485,502 | B2 | 11/2002 | Don Michael et al. |
| 6,491,712 | B1 | 12/2002 | O'Connor |
| 6,494,895 | B2 | 12/2002 | Addis |
| 6,497,709 | B1 | 12/2002 | Heath |
| 6,499,487 | B1 | 12/2002 | McKenzie et al. |
| 6,500,166 | B1 | 12/2002 | Zadno Azizi et al. |
| 6,500,191 | B2 | 12/2002 | Addis |
| 6,502,606 | B2 | 1/2003 | Klint |
| 6,506,203 | B1 | 1/2003 | Boyle et al. |
| 6,506,205 | B2 | 1/2003 | Goldberg et al. |

| | | |
|---|---|---|
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 * | 12/2003 | Roth et al. .................. 606/200 |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 * | 8/2005 | Forber .................. 606/200 |
| 6,936,059 B2 | 8/2005 | Belef |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,204,847 B1 | 4/2007 | Gambale |
| 7,220,271 B2 | 5/2007 | Clubb et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |

| | | |
|---|---|---|
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1* | 2/2002 | Demond et al. .............. 606/200 |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1* | 6/2002 | Khosravi .............. 606/200 |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1* | 8/2002 | Diaz et al. .............. 606/200 |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1* | 12/2002 | Shadduck .............. 606/200 |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucck |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |

| | | | | | | |
|---|---|---|---|---|---|---|
| 2003/0060844 A1 | 3/2003 | Borillo et al. | | 2003/0187495 A1 | 10/2003 | Cully et al. |
| 2003/0065354 A1 | 4/2003 | Boyle et al. | | 2003/0191492 A1 | 10/2003 | Gellman et al. |
| 2003/0065355 A1 | 4/2003 | Weber | | 2003/0191493 A1 | 10/2003 | Epstein et al. |
| 2003/0065356 A1 | 4/2003 | Tsugita et al. | | 2003/0195554 A1 | 10/2003 | Shen et al. |
| 2003/0069596 A1* | 4/2003 | Eskuri ............... 606/200 | | 2003/0195555 A1 | 10/2003 | Khairkhahan et al. |
| 2003/0073979 A1 | 4/2003 | Naimark et al. | | 2003/0195556 A1 | 10/2003 | Stack et al. |
| 2003/0074019 A1 | 4/2003 | Gray et al. | | 2003/0199819 A1 | 10/2003 | Beck |
| 2003/0074054 A1 | 4/2003 | Duerig et al. | | 2003/0199917 A1 | 10/2003 | Knudson et al. |
| 2003/0078614 A1 | 4/2003 | Salahieh et al. | | 2003/0199918 A1 | 10/2003 | Patel et al. |
| 2003/0083608 A1 | 5/2003 | Evans et al. | | 2003/0199919 A1 | 10/2003 | Palmer et al. |
| 2003/0083692 A1 | 5/2003 | Vrba et al. | | 2003/0199920 A1 | 10/2003 | Boylan et al. |
| 2003/0083693 A1 | 5/2003 | Daniel et al. | | 2003/0199921 A1 | 10/2003 | Palmer et al. |
| 2003/0088211 A1 | 5/2003 | Anderson et al. | | 2003/0204168 A1 | 10/2003 | Bosma et al. |
| 2003/0088266 A1 | 5/2003 | Bowlin | | 2003/0204202 A1 | 10/2003 | Palmer et al. |
| 2003/0093110 A1 | 5/2003 | Vale | | 2003/0204203 A1 | 10/2003 | Khairkhahan et al. |
| 2003/0093112 A1 | 5/2003 | Addis | | 2003/0208222 A1 | 11/2003 | Zadno-Azizi |
| 2003/0097094 A1 | 5/2003 | Ouriel et al. | | 2003/0208224 A1* | 11/2003 | Broome ............... 606/200 |
| 2003/0097145 A1 | 5/2003 | Goldberg et al. | | 2003/0208225 A1 | 11/2003 | Goll et al. |
| 2003/0100917 A1* | 5/2003 | Boyle et al. ........... 606/200 | | 2003/0208226 A1 | 11/2003 | Bruckheimer et al. |
| 2003/0100918 A1 | 5/2003 | Duane | | 2003/0208227 A1 | 11/2003 | Thomas |
| 2003/0100919 A1 | 5/2003 | Hopkins et al. | | 2003/0208228 A1 | 11/2003 | Gilson et al. |
| 2003/0105472 A1 | 6/2003 | McAlister | | 2003/0208229 A1 | 11/2003 | Kletschka |
| 2003/0105484 A1 | 6/2003 | Boyle et al. | | 2003/0208253 A1 | 11/2003 | Beyer et al. |
| 2003/0105486 A1 | 6/2003 | Murphy et al. | | 2003/0212428 A1 | 11/2003 | Richter |
| 2003/0109824 A1 | 6/2003 | Anderson et al. | | 2003/0212429 A1 | 11/2003 | Keegan et al. |
| 2003/0109897 A1 | 6/2003 | Walak et al. | | 2003/0212431 A1 | 11/2003 | Brady et al. |
| 2003/0109916 A1 | 6/2003 | Don Michael | | 2003/0212432 A1 | 11/2003 | Khairkhahan et al. |
| 2003/0114879 A1 | 6/2003 | Euteneuer et al. | | 2003/0212433 A1 | 11/2003 | Ambrisco et al. |
| 2003/0114880 A1 | 6/2003 | Hansen et al. | | 2003/0212434 A1 | 11/2003 | Thielen |
| 2003/0120303 A1 | 6/2003 | Boyle et al. | | 2003/0216774 A1 | 11/2003 | Larson |
| 2003/0120304 A1 | 6/2003 | Kaganov et al. | | 2003/0220665 A1 | 11/2003 | Eskuri et al. |
| 2003/0125764 A1 | 7/2003 | Brady et al. | | 2003/0220667 A1 | 11/2003 | Van der Burg et al. |
| 2003/0125765 A1 | 7/2003 | Blackledge et al. | | 2003/0225418 A1 | 12/2003 | Esksuri et al. |
| 2003/0130680 A1 | 7/2003 | Russell | | 2003/0225435 A1 | 12/2003 | Huter et al. |
| 2003/0130681 A1 | 7/2003 | Ungs | | 2003/0229374 A1 | 12/2003 | Brady et al. |
| 2003/0130682 A1 | 7/2003 | Broome et al. | | 2003/0233117 A1 | 12/2003 | Adams et al. |
| 2003/0130684 A1 | 7/2003 | Brady et al. | | 2004/0006364 A1 | 1/2004 | Ladd |
| 2003/0130685 A1 | 7/2003 | Daniel et al. | | 2004/0006365 A1 | 1/2004 | Brady et al. |
| 2003/0130686 A1 | 7/2003 | Daniel et al. | | 2004/0006370 A1 | 1/2004 | Tsugita |
| 2003/0130687 A1 | 7/2003 | Daniel et al. | | 2004/0015152 A1 | 1/2004 | Day |
| 2003/0130688 A1 | 7/2003 | Daniel et al. | | 2004/0039412 A1 | 2/2004 | Isshiki et al. |
| 2003/0135232 A1 | 7/2003 | Douk et al. | | 2004/0049226 A1 | 3/2004 | Keegan et al. |
| 2003/0135233 A1 | 7/2003 | Bates et al. | | 2004/0054394 A1 | 3/2004 | Lee |
| 2003/0139764 A1 | 7/2003 | Levinson et al. | | 2004/0054395 A1 | 3/2004 | Lee et al. |
| 2003/0139765 A1 | 7/2003 | Patel et al. | | 2004/0059372 A1 | 3/2004 | Tsugita |
| 2003/0144685 A1 | 7/2003 | Boyle et al. | | 2004/0064067 A1 | 4/2004 | Ward |
| 2003/0144686 A1 | 7/2003 | Martinez et al. | | 2004/0064179 A1 | 4/2004 | Linder et al. |
| 2003/0144687 A1 | 7/2003 | Brady et al. | | 2004/0068271 A1 | 4/2004 | McAlister |
| 2003/0144688 A1 | 7/2003 | Brady et al. | | 2004/0078044 A1 | 4/2004 | Kear |
| 2003/0144689 A1 | 7/2003 | Brady et al. | | 2004/0082962 A1 | 4/2004 | Demarais et al. |
| 2003/0150821 A1 | 8/2003 | Bates et al. | | 2004/0088038 A1 | 5/2004 | Dehnad et al. |
| 2003/0153935 A1 | 8/2003 | Mialhe | | 2004/0093009 A1* | 5/2004 | Denison et al. ............ 606/200 |
| 2003/0153942 A1 | 8/2003 | Wang et al. | | 2004/0093012 A1 | 5/2004 | Cully et al. |
| 2003/0153943 A1 | 8/2003 | Michael et al. | | 2004/0093016 A1 | 5/2004 | Root et al. |
| 2003/0153944 A1 | 8/2003 | Phung et al. | | 2004/0093059 A1 | 5/2004 | Lee et al. |
| 2003/0153945 A1 | 8/2003 | Patel et al. | | 2004/0098022 A1 | 5/2004 | Barone |
| 2003/0158518 A1 | 8/2003 | Schonholz et al. | | 2004/0098026 A1 | 5/2004 | Joergensen et al. |
| 2003/0158574 A1 | 8/2003 | Esch et al. | | 2004/0098033 A1 | 5/2004 | Leeflang et al. |
| 2003/0158575 A1 | 8/2003 | Boylan et al. | | 2004/0098112 A1 | 5/2004 | DiMatteo et al. |
| 2003/0163158 A1 | 8/2003 | White | | 2004/0102719 A1 | 5/2004 | Keith et al. |
| 2003/0163159 A1 | 8/2003 | Patel et al. | | 2004/0106944 A1 | 6/2004 | Daniel et al. |
| 2003/0167068 A1 | 9/2003 | Amplatz | | 2004/0116831 A1 | 6/2004 | Vrba |
| 2003/0167069 A1 | 9/2003 | Gonzales et al. | | 2004/0133232 A1 | 7/2004 | Rosenbluth et al. |
| 2003/0171769 A1 | 9/2003 | Barbut | | 2004/0138696 A1 | 7/2004 | Drasler et al. |
| 2003/0171770 A1 | 9/2003 | Kusleika et al. | | 2004/0153118 A1 | 8/2004 | Clubb et al. |
| 2003/0171771 A1 | 9/2003 | Anderson et al. | | 2004/0158278 A1 | 8/2004 | Becker et al. |
| 2003/0171772 A1 | 9/2003 | Amplatz | | 2004/0162576 A1 | 8/2004 | Barbut et al. |
| 2003/0171800 A1 | 9/2003 | Bicek et al. | | 2004/0164030 A1 | 8/2004 | Lowe et al. |
| 2003/0171803 A1 | 9/2003 | Shimon | | 2004/0167567 A1 | 8/2004 | Cano et al. |
| 2003/0176884 A1 | 9/2003 | Berrada et al. | | 2004/0176794 A1* | 9/2004 | Khosravi ............... 606/200 |
| 2003/0176885 A1 | 9/2003 | Broome et al. | | 2004/0176833 A1 | 9/2004 | Pavcnik et al. |
| 2003/0176886 A1 | 9/2003 | Wholey et al. | | 2004/0199203 A1 | 10/2004 | Oslund et al. |
| 2003/0176887 A1 | 9/2003 | Petersen | | 2004/0204737 A1 | 10/2004 | Boismier et al. |
| 2003/0176888 A1 | 9/2003 | O'Connell | | 2004/0215322 A1 | 10/2004 | Kerr |
| 2003/0176889 A1 | 9/2003 | Boyle et al. | | 2004/0225321 A1 | 11/2004 | Krolik et al. |
| 2003/0181942 A1 | 9/2003 | Sutton et al. | | 2004/0236369 A1 | 11/2004 | Dubrul |
| 2003/0181943 A1 | 9/2003 | Daniel et al. | | 2005/0004663 A1 | 1/2005 | Llanos et al. |
| 2003/0187474 A1 | 10/2003 | Keegan et al. | | 2005/0021125 A1 | 1/2005 | Stack et al. |
| 2003/0187475 A1 | 10/2003 | Tsugita et al. | | 2005/0027345 A1 | 2/2005 | Horan et al. |

| | | |
|---|---|---|
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 * | 9/2005 | Brady et al. .................. 606/200 |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82, 2727 (2003), pp. 2727.

* cited by examiner

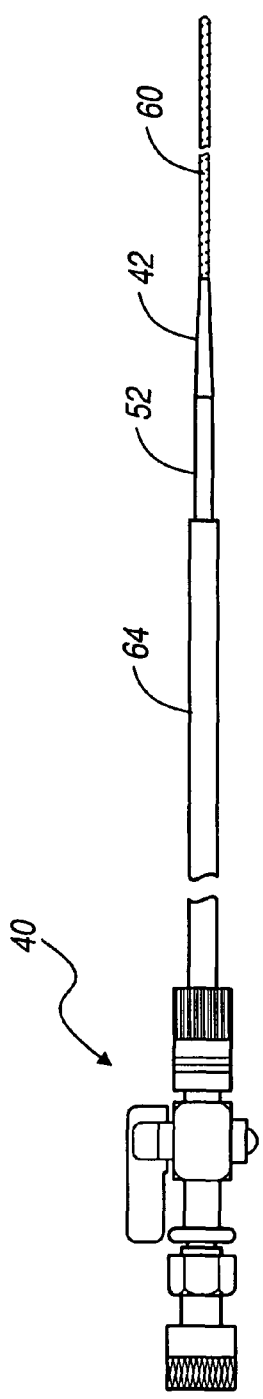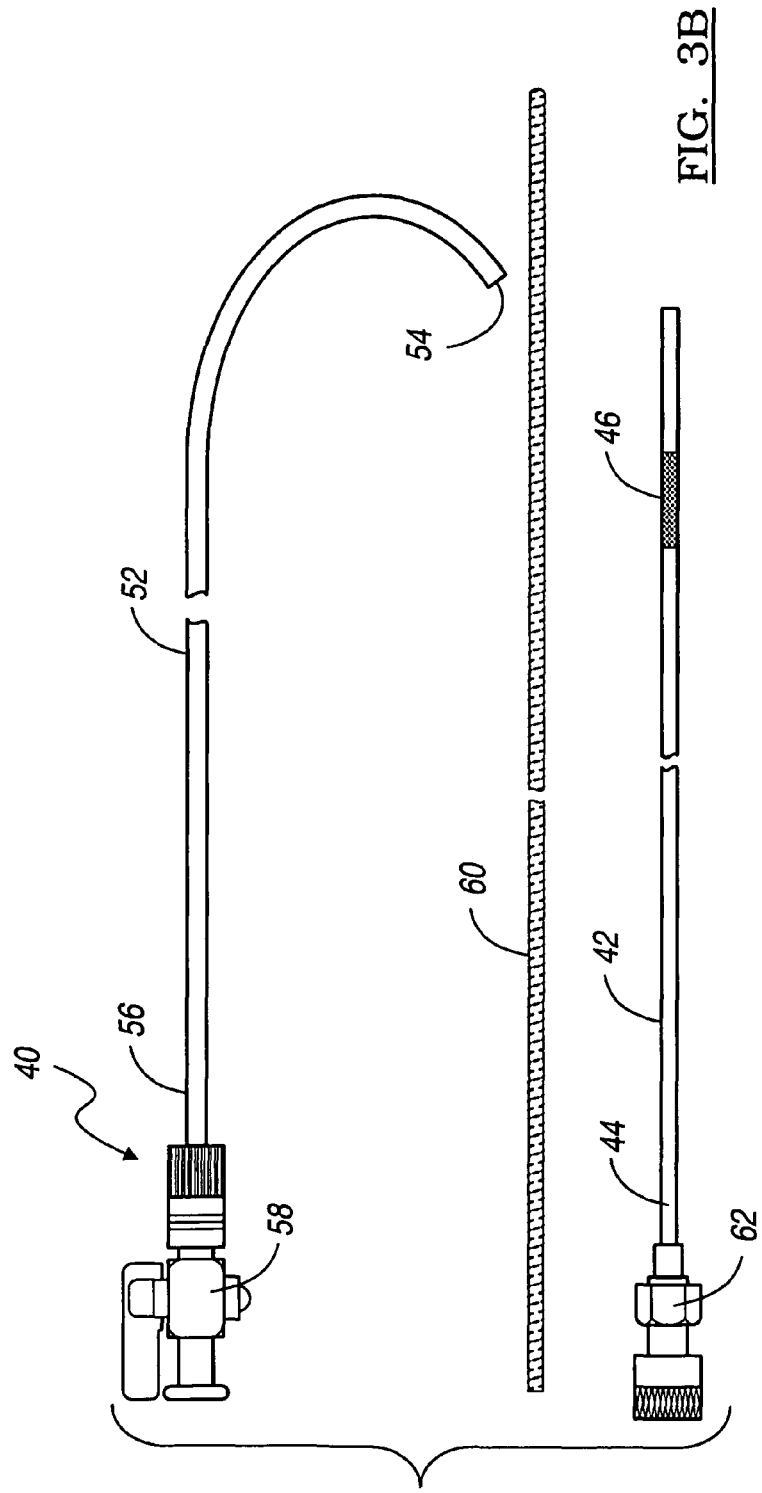

2

EMBOLIC PROTECTION DEVICE

CROSS REFERENCE TO RELATED APPLICATIONS

This application claims the benefit of U.S. provisional application 60/718,171, filed Sep. 16, 2005 which is incorporated by reference herein.

BACKGROUND

1. Field of the Invention

The present invention generally relates to a medical device for embolic protection.

2. Description of Related Art

With the continuing advance of medical techniques, interventional procedures are more commonly being used to actively treat stenosis, occlusions, lesions, or other defects within a patient's blood vessels. Often the treated regions are in the coronary, carotid or even cerebral arteries. One procedure for treating an occluded or stenosed blood vessel is angioplasty. During angioplasty, an inflatable balloon is introduced into the occluded region. The balloon is inflated, pushing against the plaque or other material of the stenosed region and increasing the intralumenal diameter of the vessel. As the balloon presses against the material, portions of the material may inadvertently break free from the plaque deposit. These emboli may travel along the vessel and become trapped in a smaller blood vessel restricting blood flow to a vital organ, such as the brain.

Other methods for removing plaque or thrombus from arteries may include mechanical ablation, or non-contact ablation using light waves, sound waves, ultrasonics, or other radiation. Each of these methods are subject to the risk that some thrombogenic material may dislodge from the wall of the vessel and occlude a smaller blood vessel. The occlusion may cause damage to the patient, including an ischemic stroke in the cerebral arteries.

To prevent the risk of damage from emboli, many devices have been used to restrict the flow of emboli downstream from the stenosed area. One method includes inserting a balloon that may be expanded to occlude the flow of blood through the artery downstream of the stenosed area. An aspirating catheter may be located between the balloon and stenosed area and used to remove emboli that may be caused by the treatment. However, because the balloon completely blocks blood flow through the vessel, the vessel may be occluded only for short periods of time, limiting use of the procedure.

As an alternative to occluding flow through the blood vessel, various filtering devices have been proposed. Such devices typically have elements that form legs or a mesh that capture embolic material, but allow blood cells to flow between the elements. Capturing the emboli in the filter device prevents the material from being lodged downstream in a smaller blood vessel. The filter may then be removed along with the embolic material after the procedure has been performed and the risk from emboli has decreased.

Challenges also exist with filtering devices. Often it is desirable to deploy filter devices from the proximal side of a stenosis. Therefore, the profile of the filtering device should be smaller than the opening in the stenosed vessel. In addition, if the filter portion is not held against the inside of the vessel wall, there is a risk that embolic material may pass between the filter and the vessel wall.

In view of the above, it is apparent that there exists a need for an improved medical device for embolic protection.

SUMMARY

In satisfying the above need, as well as overcoming the enumerated drawbacks and other limitations of the related art, the present invention provides an improved medical device for embolic protection.

The embolic protection device includes a basket formed from flexible struts. The struts extend from a first end of the basket to the second end of the basket. In addition, the struts form a middle portion of the basket where the struts extend substantially perpendicular to a longitudinal axis running between the first and second end of the basket.

The embolic protection device also includes a filter portion attached to the struts that extends between the middle portion of the basket and the second end of the basket. The struts being biased into an expanded state such that the middle portion of the basket forces the filter portion against an inner wall of the vessel. The embolic protection device also includes a core wire extending between the first and second ends of the basket. The core wire may be moved relative to the struts forcing the basket into a contracted state.

The struts extend from the first and second ends substantially parallel to the core wire. Between the ends and the middle portion of the basket, the struts extend helically. Accordingly the struts form a smooth continuous transition between the parallel portion at the ends and the middle portion of the basket. In the middle portion of the basket, the struts extend perpendicular to the longitudinal axis for a distance according to the relationship $d=\pi D/(2n)$, such that the struts collectively form a circle, substantially around the circumference of the basket.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 3a is a side view of an embolic protection assembly for capturing emboli during treatment of a stenotic lesion in accordance with one embodiment of the present invention;

FIG. 3b is an exploded side view of the assembly in FIG. 3a;

DETAILED DESCRIPTION

Figure 1:
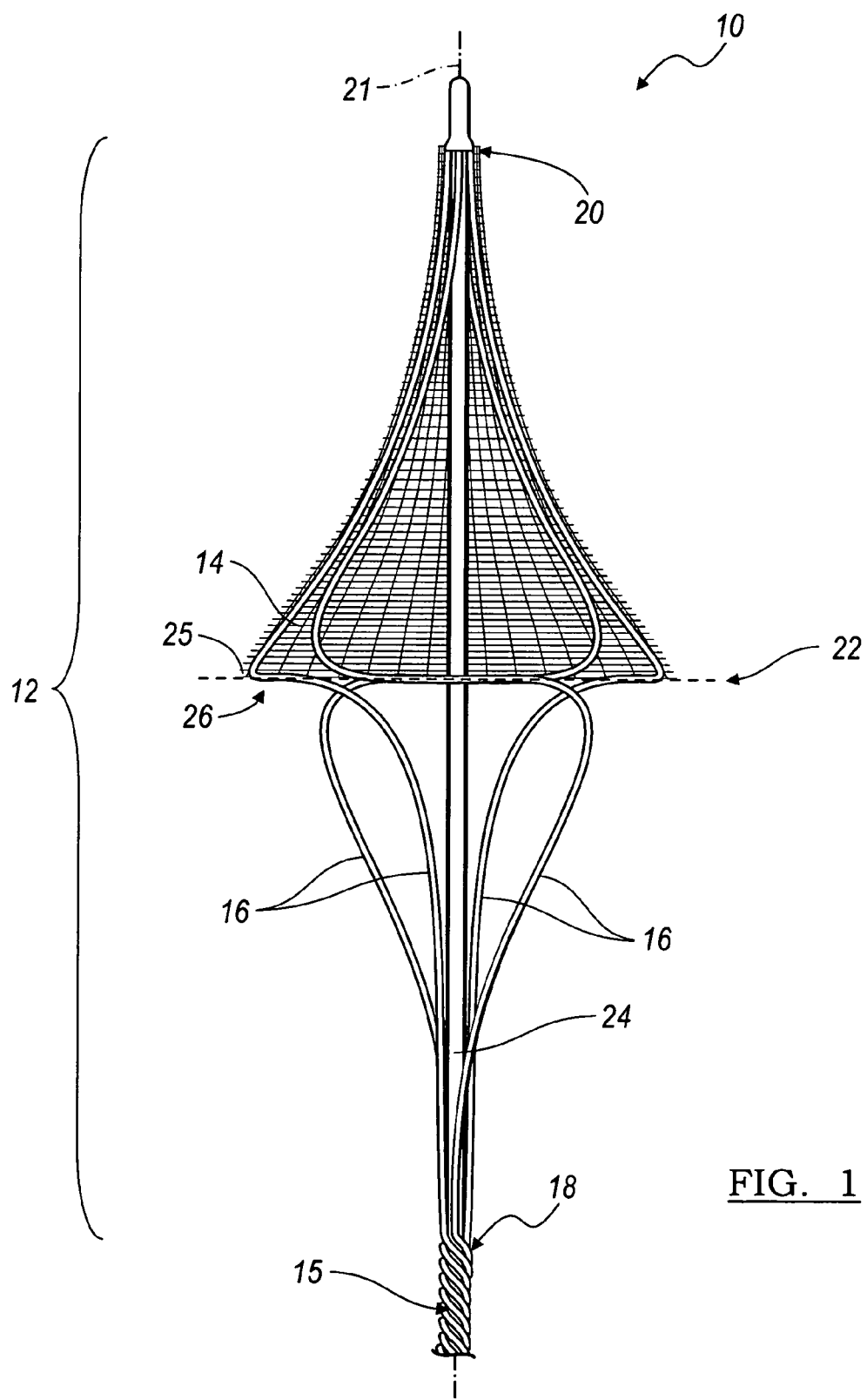
FIG. 1 is a side view of a medical device in accordance with the present invention.
Figure 2:
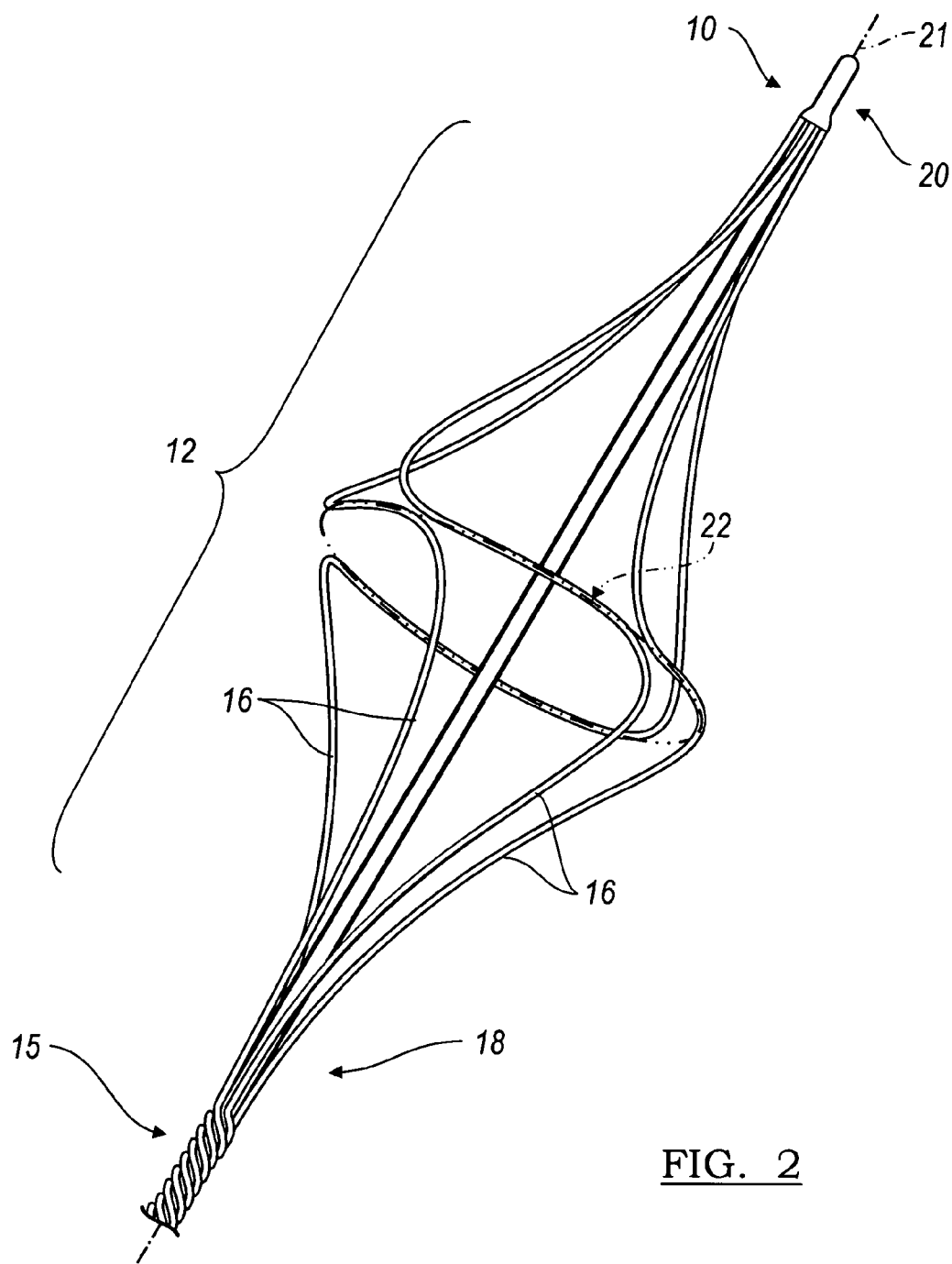
FIG. 2 is an perspective view of the medical device in FIG. 1.

Referring now to FIGS. 1 and 2, the medical device 10 includes a basket 12 and a stem 15. The basket 12 includes a filter portion 14 and a plurality of struts 16. The struts 16 extend between a first end 18 and a second end 20 of the basket 12. The basket 12 also includes a middle portion 22 where the struts 16 are substantially perpendicular to a longitudinal axis 21 of the basket 12 extending between the first and second ends 18, 20. The middle portion 22 supports the outer edges of the filter portion 14 against the inside of a vessel.

The struts 16 may be comprised of any suitable material such as a superelastic material, stainless steel wire, cobalt-chromium-nickel-molybdenum-iron alloy, or cobalt-chrome alloy. It is understood that the struts 16 may be formed of any other suitable material that will result in a self-opening or self-expanding basket, such as shape memory alloys. Shape memory alloys have the desirable property of becoming rigid, that is, returning to a remembered state, when heated above a transition temperature. A shape memory alloy suitable for the present invention is Ni-Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the struts 16 are made from Nitinol with a transition temperature that is slightly below normal body temperature of humans, which is about 98.6° F. Thus, when the basket 12 is deployed in a body vessel and exposed to normal body temperature, the alloy of the struts 16 will transform to austenite, that is, the remembered state, which for one embodiment of the present invention is the expanded configuration when the basket 12 is deployed in the body vessel. To facilitate removal of the basket 12, the struts 16 are cooled to transform the material to martensite which is more ductile than austenite, making the struts 16 more malleable. As such, the basket 12 can be more easily collapsed and pulled into a lumen of a catheter for removal.

In another embodiment, the struts 16 are made from Nitinol with a transition temperature that is above normal body temperature of humans, which is about 98.6° F. Thus, when the basket 12 is deployed in a body vessel and exposed to normal body temperature, the struts 16 are in the martensitic state so that the basket 12 is sufficiently ductile to bend or form into a desired shape, which for the present invention is an expanded configuration. To facilitate removal of the basket 12, the struts 16 are heated to transform the alloy to austenite so that the basket 12 becomes rigid and returns to a remembered state, which for the basket 12 is a collapsed configuration.

Accordingly, the filter portion 14 is attached to the middle portion 22 and the second end 20 of the basket 12. The filter portion 14 has a lip 25 attached to the middle portion 22 of the basket 12, defining an opening 26 of the filter portion 14 when the basket 12 is in the expanded state for capturing emboli. The lip 25 may be attached to the middle portion 22 by any suitable means including sonic bonding, thermal bonding, or adhesive bonding. The filter portion 14 extends from the lip 34 to the second end 20 of the basket 12 to form a proximally facing concave shape. The opening 26 of the filter portion 14 is configured to face toward the stenotic lesion.

The filter portion 14 may be made of a mesh or porous sheet. The filter 14 includes openings large enough to allow the passage of blood cells therethrough, but small enough to prevent the passage of embolic material. The filter portion 14 may be comprised of any suitable material to be used for capturing emboli from the stenotic lesion during treatment thereof. In one embodiment, the filter portion 14 is made of connective tissue material for capturing emboli. In this embodiment, the connective tissue comprises extracellular matrix (ECM). As known, ECM is a complex structural entity surrounding and supporting cells that are found within mammalian tissues. More specifically, ECM comprises structural proteins (e.g., collagen and elastin), specialized protein (e.g., fibrillin, fibronectin, and laminin), and proteoglycans, a protein core to which are attached are long chains of repeating disaccharide units termed of glycosaminoglycans.

Most preferably, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, SIS is used to temporarily adhere the filter portion 14 to the walls of a body vessel in which the device 10 is deployed. SIS has a natural adherence or wettability to body fluids and connective cells comprising the connective tissue of a body vessel wall. Due to the temporary nature of the duration in which the device 10 is deployed in the body vessel, host cells of the wall will adhere to the filter portion 14 but not differentiate, allowing for retrieval of the device 10 from the body vessel.

In other embodiments, the filter portion 14 may also be made of a mesh/net cloth, nylon, polymeric material, Teflon, metal, or shape memory alloy or woven mixtures thereof without falling beyond the scope or spirit of the present invention.

The basket 12 also includes a core wire 24 that extends from the second end 20 through the first end 18 of the basket 12. The struts 16 are biased into an expanded state providing a radial force to support the filter portion 14 against an inner wall of the vessel. Accordingly, the core wire 24 may be moved distally relative to the struts 16, such that the struts 16 will be pulled tight against the core wire 24 causing the filter portion 14 to collapse and fold between the struts 16. Drawing the filter portion 14 tightly against the core wire 24 minimizes the diameter of the medical device 10 for insertion.

The struts 16 are spirally wound around the core wire 24 along the stem portion 15 of the medical device 10. Accordingly, the struts 16 form a lumen that slidably engages the core wire 24. At the first end 18 of the basket 12, the struts 16 are substantially parallel to the longitudinal axis 21 and the core wire 24. The struts 16 extend between the first end 18 and the middle portion 22 in a helical and radially symmetric fashion with one another. Between the first end 18 and the middle portion 22, the struts 16 form a smooth continuous transition, such that the struts 16 extend radially from the longitudinal axis 21. Across the middle portion 22 of the basket 12, the struts 16 extend at least substantially perpendicular to the longitudinal axis 21 and the core wire 24 around a portion of the circumference of the basket 12. Each of the struts 16 cooperate to outline a circle substantially along the circumference of the middle portion 22 that is perpendicular to the longitudinal axis 21. As such, the struts 16 extend perpendicular to the longitudinal axis 21 for a distance according to the relationship $d=\pi D/(2n)$; where d is the distance that the struts 16 travel perpendicular to the longitudinal axis 21, D is the cross sectional diameter of the middle portion 22 in its fully expanded state, and n is a number of struts 16 that extend from the first end 18 to the middle portion 22 of the basket 12.

The struts 16 also form a smooth continuous transition between the middle portion 22 of the basket 12 and the second end 20, such that the struts gradually extend radially towards the longitudinal axis 21 from the middle portion 22. At the second end 20, the struts 16 are, again, substantially parallel to the longitudinal axis 21 and the core wire 24. The struts 16 may be attached to the second end 20 by any suitable means, such as a cap or bonding including but not limited to sonic bonding, thermal bonding, or adhesive bonding. The struts 16 and the filter portion 14 may be attached to each other and the core wire 24 at the second end 20. In addition, the filter portion 14 is also attached to the struts 16 across the middle portion 22 of the basket 12. Further, the filter portion 14 may be attached along the struts 16 between the middle portion 22 and the second end 20. Attachment of the filter portion 14 to the struts 16 may be achieved by any suitable means including sonic bonding, thermal bonding, or adhesive bonding. The distance traveled circumferentially along the apparent circle in the middle portion 22, per the formula $\pi D/(2n)$, facilitates firm circumferential support of the filter portion 14 against the inner wall of a vessel due to a radial force provided by the middle portion 22. In addition, the filter portion 14 collapses or folds between the struts 16 of the basket 12.

In use, the device 10 expands from the collapsed state to the expanded state, engaging the basket 12 with the body vessel. In turn, the lip 25 of the filter portion 14 expands to open the filter portion 14 for capturing emboli during treatment of the stenotic lesion. After the need for such device 10 in the vasculature passes, the device 10 may be retrieved.

FIGS. 3a and 3b depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device mentioned above. The tubular body 44 is preferably made of soft flexible material such as silicon or any other suitable material. In this embodiment, the balloon catheter 42 includes an outer lumen and an inner lumen. The outer lumen is in fluid communication with the balloon 46 for inflating and deflating the balloon 46. The inner lumen is formed therethrough for percutaneous guidance through the body vessel.

As shown, the assembly 40 further includes an inner catheter 52 having a distal end 54 through which the balloon catheter 42 is disposed for deployment in the body vessel. The inner catheter 52 is preferably made of a soft, flexible material such as silicon or any other suitable material. Generally, the inner catheter 52 further has a proximal end 56 and a plastic adaptor or hub 58 to receive the embolic protection device and balloon catheter 42 to be advanced therethrough. The size of the inner catheter 52 is based on the size of the body vessel in which it percutaneously inserts, and the size of the balloon catheter 42.

As shown, the assembly 40 may also include a wire guide 60 configured to be percutaneously inserted within the vasculature to guide the inner catheter 52 to a location adjacent a stenotic lesion. The wire guide 60 provides the inner catheter 52 (and balloon catheter 42) a path during insertion within the body vessel. The size of the wire guide 60 is based on the inside diameter of the inner catheter 52.

In one embodiment, the balloon catheter 42 has a proximal fluid hub 62 in fluid communication with the balloon 46 via the outer lumen for fluid to be passed therethrough for inflation and deflation of the balloon 46 during treatment of the stenotic lesion.

As shown, the embolic protection device is coaxially disposed through the inner lumen of the balloon catheter 42 prior to treatment of the stenotic lesion in the body vessel. The distal protection device is guided through the inner lumen preferably from the hub 58 and distally beyond the balloon 46 of the balloon catheter 42, exiting from the distal end of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 52 in a body vessel. Of course, any other suitable material may be used without falling beyond the scope or spirit of the present invention. The introducer sheath 64 may have any suitable size, e.g., between about three-french to eight-french. The introducer serves to allow the inner and balloon catheters 42 to be percutaneously inserted to a desired location in the body vessel. The introducer sheath 64 receives the inner catheter 52 and provides stability to the inner catheter at a desired location of the body vessel. For example, the introducer sheath 64 is held stationary within a common visceral artery, and adds stability to the inner catheter 52, as the inner catheter 52 is advanced through the introducer sheath 64 to a dilatation area in the vasculature.

When the distal end 54 of the inner catheter 52 is at a location downstream of the dilatation area in the body vessel, the balloon catheter 42 is inserted therethrough to the dilatation area. The device 10 is then loaded at the proximal end of the balloon catheter 42 and is advanced through the inner lumen thereof for deployment through its distal end. In this embodiment, the proximal stem is used to mechanically advance or push the device 10 through the catheter.

Figure 4:
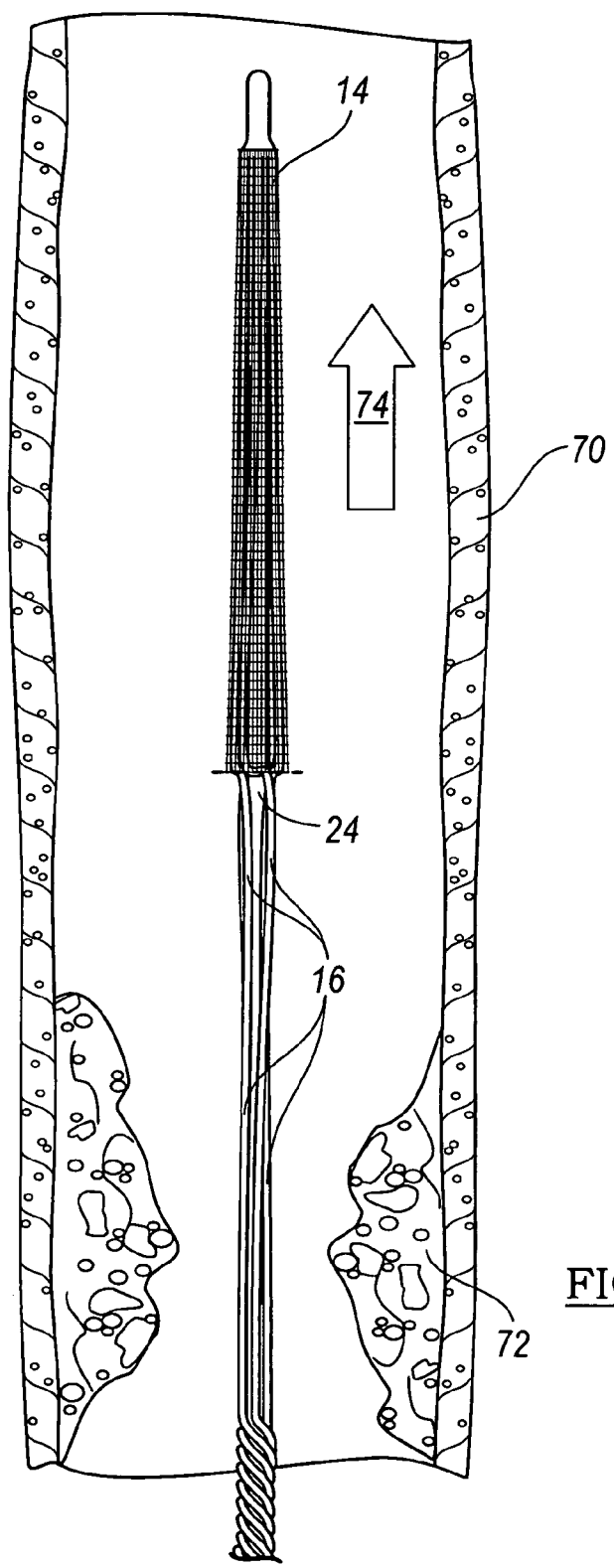
FIG. 4 is a sectional view of a blood vessel illustrating insertion of the medical device of FIG. 1 in the collapsed state.

Now referring to FIG. 4, a cutaway view of a vessel 70 is provided illustrating insertion of the medical device 10. The medical device 10 is inserted with the basket 12 in a collapsed state, allowing the medical device 10 to navigate through the narrow opening formed by the stenosed area 72. Accordingly, during insertion, the profile of the medical device 10 should be minimized. As such, the core wire 24 is moved distally relative to the struts 16, thereby drawing the struts 16 and the filter portion 14 tightly against the core wire 24 and forming a collapsed state. The medical device 10 is inserted into the vessel 70 past the stenosis 72 as denoted by the distally pointing arrow 74.

Figure 5:
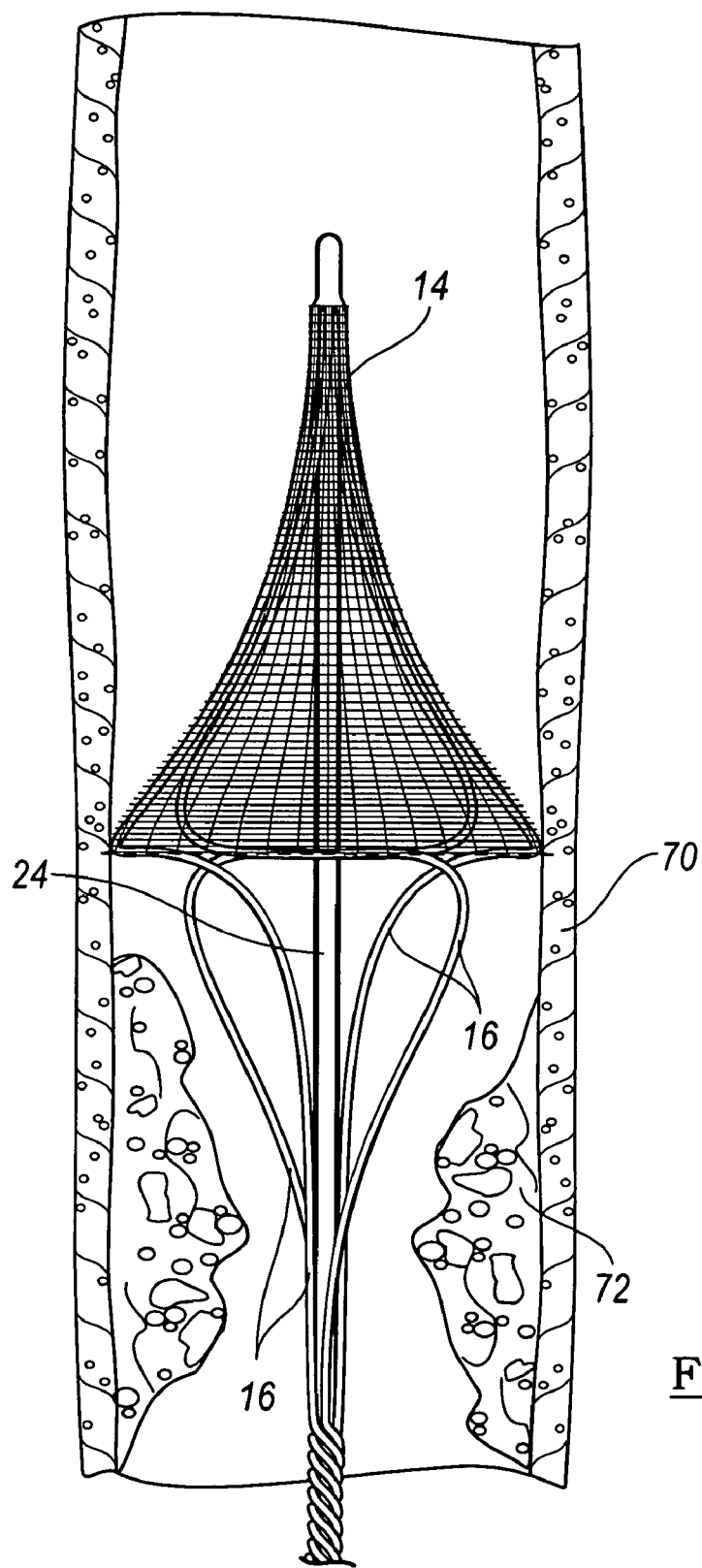
FIG. 5 is a sectional view of the blood vessel illustrating the medical device of FIG. 1 in a fully deployed state.
Figure 6:
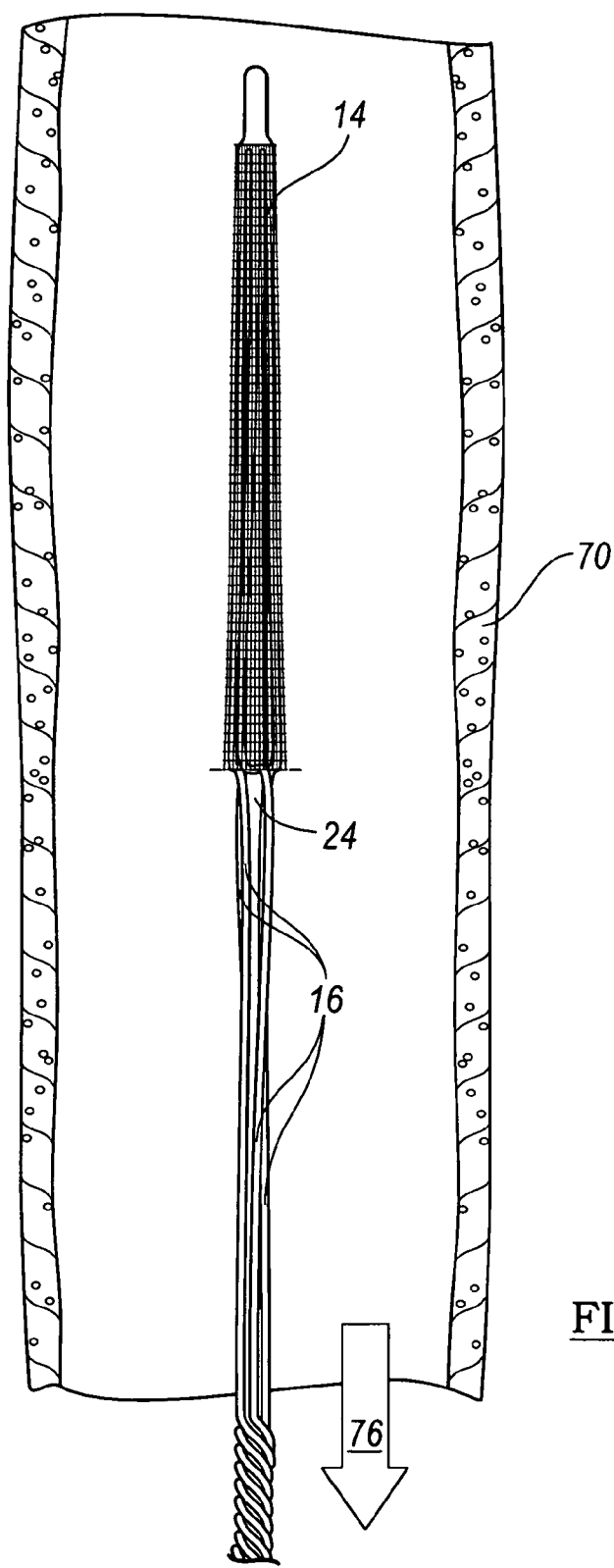
FIG. 6 is a sectional view of the blood vessel illustrating removal of the medical device from the vessel.

Once the basket portion 12 of the medical device 10 is located distal the stenosis 72, the basket portion 12 can be expanded against the inner wall of the blood vessel 70 as shown in FIG. 5. In the expanded state, the struts 16 provide a radial force against the filter portion 14, thereby securing the filter portion 14 against the inner wall of the vessel 70. The radial force eliminates gaps between the filter portion 14 and the vessel 70 forcing embolic material that is released from the stenosis 72 to be trapped downstream in the filter portion 14. After a procedure is performed on the stenosis 72, the core wire 24 is moved distally relative to the struts 16 to collapse the struts 16 and filter portion 14 tightly against the core wire 24, as shown in FIG. 6. In the collapsed state, the emboli are trapped within the filter portion 14 and against the core wire 24. However, a catheter may also be slid over the medical device 10, as a precautionary measure during removal. The medical device 10 in the collapsed state, may then be removed proximally, as denoted by proximally pointing arrow 76.

Figure 7:
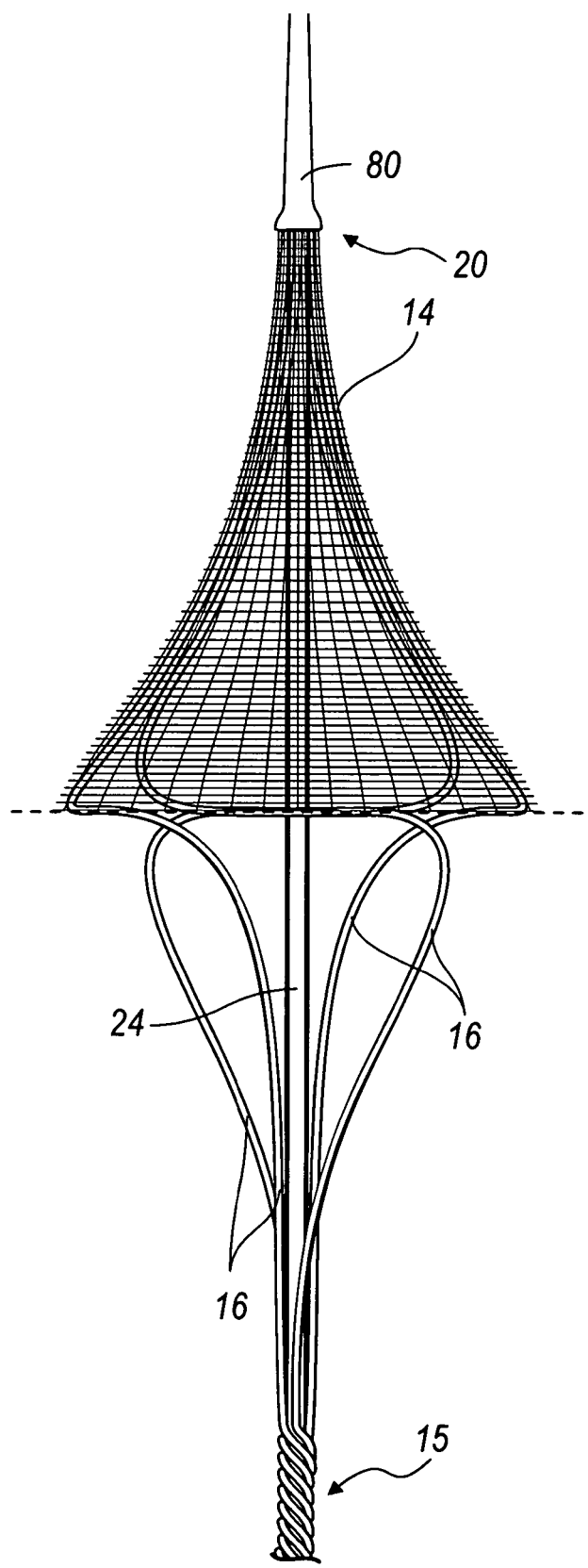
FIG. 7 is a side view of another embodiment of the present invention including a floppy tip.

Now referring to FIG. 7, the medical device 10 may include a floppy tip 80 located distal the second end 20 of the basket 12 to provide additional guidance during insertion. The floppy tip 80 may extend from the second end 20 and may include a hydrophilic or other lubricious coating to facilitate easy advancement of the medical device to and through the stenosed region of the blood vessel during insertion. The floppy tip 80 is attached to the second end 20, for example by adhesive bonding, and may be made of nylon, polymeric material, silicone, Teflon, or other commonly known material without falling beyond the scope or spirit of the present invention. The flexibility provided by the floppy tip, aids in advancement of the medical device through the vessel while minimizing any trauma caused during the advancement.

Figure 8:
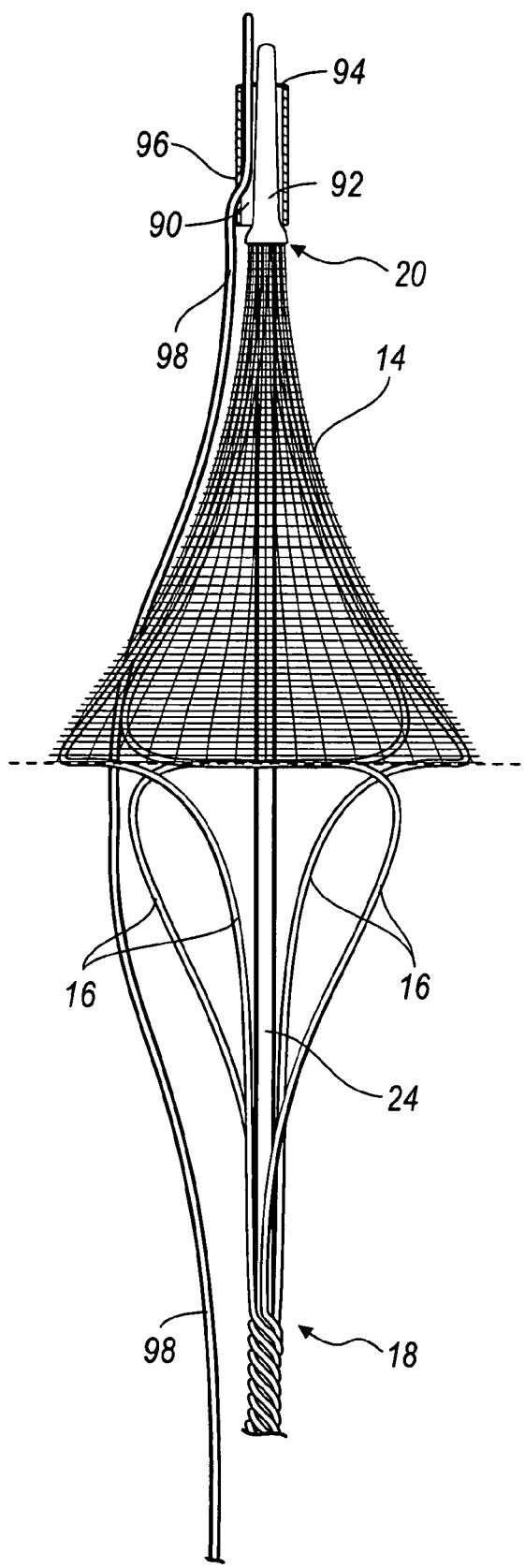
FIG. 8 is a side view of yet another embodiment of the present invention including a guide wire adapter.

Now referring to FIG. 8, another embodiment of a medical device in accordance with the present invention is provided. A tubular member 90 may be located on a tip 92 or in lieu of the tip extending distally from the second end 20 of the basket portion 12. The tubular member 90 may be made of nylon, polymeric material, Teflon, superelastic metal or other commonly known material without falling beyond the scope or spirit of the present invention. The tubular member 90 may include a first opening 94 and a second opening 96 such that a wire guide 98 may extend through the first and second opening 94, 96 of the tubular member 90. Accordingly, the tubular member 90 allows the medical device 10 to be guided along the wire guide 98 or alternatively allowing the wire guide 98 to be advanced together with the medical device 10 during insertion.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

I claim:

1. An embolic protection device for use in a vessel, the embolic protection device comprising:
    a basket having a first end and a second end, a longitudinal axis of the basket extending between the first end and second end, a middle portion of the basket being located between the first end and second end, the basket including a plurality of struts, the plurality of struts extending radially from the first end to the middle portion; the struts extending a distance that is at least substantially perpendicular to the longitudinal axis in order to form a circle substantially along the circumference of the middle portion; the plurality of struts extending from the circumference of the middle portion to the second end toward the longitudinal axis, the plurality of struts comprising four struts, wherein the basket is movable between an expanded state and a collapsed state;
    a filter portion attached to the plurality of struts along the circumference of the middle portion and extending between the middle portion and the second end of the basket, wherein the filter portion is attached along the plurality of struts between the middle portion and the second end, the filter portion having a distally facing concave shape when the basket is in the expanded state; and
    a core wire extending from the second end and between the first end and the second end, wherein the plurality of struts and the filter portion are attached to each other and to the core wire at the second end;
    wherein the core wire is slidable distally relative to the plurality of struts to force the basket into the collapsed state;
    wherein in the expanded state the plurality of struts provide a radial force to support the filter portion.

2. The embolic protection device according to claim 1, wherein the plurality of struts are biased into the expanded state.

3. The embolic protection device according to claim 1, wherein the plurality of struts extend from the first end substantially parallel to the longitudinal axis.

4. The embolic protection device according to claim 3, wherein the plurality of struts extend from the second end substantially parallel to the longitudinal axis.

5. The embolic protection device according to claim 3, wherein the plurality of struts extend perpendicular to the longitudinal axis for a distance according to the relationship $d=\pi D/(2n)$; where d is the distance that the plurality of struts travel perpendicular to the longitudinal axis, D is a cross sectional diameter of the basket, and n is a number of struts forming the basket.

6. The embolic protection device according to claim 1, further comprising a tubular portion attached to the second end, the tubular portion being configured to receive a wire guide through the tubular portion.

7. The embolic protection device according to claim 1, wherein the plurality of struts extend helically between the first end and the middle portion of the basket.

8. The embolic protection device according to claim 1, wherein the plurality of struts extend helically between the second end and the middle portion of the basket.

9. The embolic protection device according to claim 1, wherein the filter portion is made of a mesh material.

10. The embolic protection device according to claim 1, wherein the filter portion is made of a porous sheet material.

11. The embolic protection device according to claim 1, wherein the plurality of struts are formed of a shape memory material.

12. The embolic protection device according to claim 1, wherein middle portion of the basket is configured to provide a radial force sealing the filter portion against an inner wall of the vessel.

13. An embolic protection device for use in a vessel, the embolic protection device comprising:
    a basket having a first end and a second end, a longitudinal axis of the basket extending between the first and second end, a middle portion of the basket being located between the first end and second end, the basket including a plurality of struts, the plurality of struts extending from the first end to the second end, the plurality of struts extending radially from the first end to form a circle substantially along the circumference of the middle portion, the struts extending a distance in the middle portion that is substantially perpendicular to the longitudinal axis, the plurality of struts extending from the circumference of the middle portion to the second end toward the longitudinal axis, the basket being moveable between an expanded state and a collapsed state;
    a filter portion attached to the plurality of struts along the circumference of the middle portion and extending between the middle portion and the second end of the basket, wherein the filter portion is attached along the plurality of struts between the middle portion and the second end, the filter having a distally facing concave shape when the basket is in the expanded state, the plurality of struts providing a radial force to support the filter portion in the expanded state; and a core wire extending between the first end and the second end wherein the plurality of struts are spirally wound at the first end of the basket forming a lumen, the wire core extending through the lumen, wherein the plurality of struts and the filter portion are attached to each other and to the core wire at the second end, wherein the core wire is slidable distally relative to the plurality of struts to force the basket into the collapsed state; and wherein the plurality of struts extend helically between the first and second end of the basket, and the middle portion of the basket is biased to provide a radial force sealing the filter portion against an inner wall of the vessel.

14. An embolic protection assembly for capturing emboli during treatment of a stenotic lesion in a body vessel, the assembly comprising:

a balloon catheter having a tubular body portion and an expandable balloon attached to and in fluid communication with the tubular body portion for angioplasty at the stenotic lesion, the expandable balloon having distal and proximal portions; and an embolic protection device coaxially disposed within the balloon catheter during treatment of the stenotic lesion in the body vessel, the device comprising:

a basket having a first end and a second end, a longitudinal axis of the basket extending between the first and second end, a middle portion of the basket being located between the first end and second end, the basket including a plurality of struts, the plurality of struts extending a distance from the first end to the middle portion that is at least substantially perpendicular to the longitudinal axis in order to form a circle substantially along the circumference of the middle portion, the plurality of struts extending from the circumference of the middle portion to the second end toward the longitudinal axis, the basket being moveable between an expanded state and a collapsed state;

a filter portion attached to the struts along the circumference of the middle portion and extending between the middle portion and the second end of the basket, wherein the filter portion is attached along the plurality of struts between the middle portion and the second end, the filter having a distally facing concave shape when the basket is in the expanded state, the plurality of struts providing a radial force to support the filter portion in the expanded state; and a core wire extending from the second end, wherein the plurality of struts and the filter portion are attached to each other and to the core wire at the second end, wherein the core wire is slidable distally relative to the plurality of struts to force the basket into the collapsed state.

15. The embolic protection device according to claim 1, wherein the circle lies on a two-dimensional geometrical plane.

16. The embolic protection device according to claim 1, wherein the filter portion being attached along the plurality of struts between the middle portion and the second end comprises the filter portion being bonded along the plurality of struts between the middle portion and the second end.

17. The embolic protection device according to claim 6, further comprising a floppy tip attached to the second end, wherein the tubular member is located on the floppy tip.

18. The embolic protection device according to claim 17, further comprising a wire guide that extends through the tubular member.

\* \* \* \* \*

UNITED STATES PATENT AND TRADEMARK OFFICE
CERTIFICATE OF CORRECTION

| | |
|---|---|
| PATENT NO. | : 8,377,092 B2 |
| APPLICATION NO. | : 11/520109 |
| DATED | : February 19, 2013 |
| INVENTOR(S) | : Magnuson |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1049 days.

Signed and Sealed this
Eighteenth Day of November, 2014

Michelle K. Lee
*Deputy Director of the United States Patent and Trademark Office*